United States Patent

Takano et al.

[11] Patent Number: 5,844,249
[45] Date of Patent: Dec. 1, 1998

[54] APPARATUS FOR DETECTING DEFECTS OF WIRES ON A WIRING BOARD WHEREIN OPTICAL SENSOR INCLUDES A FILM OF POLYMER NON-LINEAR OPTICAL MATERIAL

[75] Inventors: Yusuke Takano, Tokyo; Shizuo Ogura, Tsurugasima; Tsunetoshi Sugiyama, Matsuyama; Wen-Bing Kang, Tokorozawa, all of Japan

[73] Assignee: Hoechst Aktiengesellschaft, Frankfurt, Germany

[21] Appl. No.: 779,571

[22] Filed: Jan. 7, 1997

Related U.S. Application Data

[63] Continuation of Ser. No. 663,295, filed as PCT/JP94/02189 Dec. 22, 1994, abandoned.

[30] Foreign Application Priority Data

Dec. 24, 1993 [JP] Japan ................................ 5-328082
May 2, 1994 [JP] Japan ................................ 6-93396

[51] Int. Cl.⁶ .................................................. G01N 21/86
[52] U.S. Cl. .............................. 250/559.34; 250/559.45; 250/559.46; 250/225; 356/237
[58] Field of Search ........................... 250/214.1, 214 R, 250/225, 559.34, 559.42, 559.44, 559.46, 559.48, 559.45; 356/237

[56] References Cited

U.S. PATENT DOCUMENTS

| | | | |
|---|---|---|---|
| 5,032,735 | 7/1991 | Kobayashi et al. | 250/559.34 |
| 5,126,660 | 6/1992 | Harvey et al. | 324/752 |
| 5,171,803 | 12/1992 | Walton et al. | 526/243 |
| 5,278,012 | 1/1994 | Yamanaka et al. | 356/237 |
| 5,334,710 | 8/1994 | Ahlheim et al. | 534/852 |
| 5,359,203 | 10/1994 | Hashii et al. | 250/559.46 |
| 5,447,662 | 9/1995 | Herr et al. | 252/582 |
| 5,715,052 | 2/1998 | Fujino et al. | 250/559.45 |
| 5,717,198 | 2/1998 | Broude et al. | 356/237 |

FOREIGN PATENT DOCUMENTS

| | | |
|---|---|---|
| 42 13 155 | 11/1992 | Germany . |
| 42 13 155 A1 | 11/1992 | Germany . |
| 4-37825 | 2/1992 | Japan . |
| 5-87839 | 4/1993 | Japan . |
| WO 91/03683 | 3/1991 | WIPO . |
| WO91/03683 | 3/1991 | WIPO . |

Primary Examiner—Stephone B. Allen
Attorney, Agent, or Firm—Frommer, Lawrence & Haug LLP

[57] ABSTRACT

A detecting apparatus capable of supporting even narrow wire widths and of detecting defects of wires in a non-contact manner is provided. The detecting apparatus comprises an optical sensor, a sensor head, and a signal processing unit. The optical sensor comprises a transparent substrate, a transparent electrode disposed on the transparent substrate, a thin film of a polymer non-linear optical material disposed on the transparent electrode, and a reflective film disposed on the thin film, and is positioned in close approximation to and without contacting an electrode to be measured on the wiring board. The sensor head comprises a light source, optical means for guiding light from the light source into the optical sensor, and detecting means for detecting reflected light from the optical sensor. The detecting means supplies the signal processing unit with a signal corresponding to the intensity of the reflected light when the electrode on the wiring board is applied with a voltage.

17 Claims, 7 Drawing Sheets

APPARATUS FOR DETECTING DEFECTS OF WIRES ON A WIRING BOARD WHEREIN OPTICAL SENSOR INCLUDES A FILM OF POLYMER NON-LINEAR OPTICAL MATERIAL

This application is a continuation of application Ser. No. 08/663,295, filed Jun. 21, 1996, as the National Phase of PCT/JP94/02189, filed Dec. 22, 1994, designating the U.S. application Ser. No. 08/663,295, now abandoned, is a continuation of, is based upon, and claims priority from, PCT Application PCT/JP94/02189, filed Dec. 22, 1994, designating the U.S., claiming priority from Japanese applications Hei-5-328082 filed on Dec. 24, 1993 and Hei-6-93396 filed on May 2, 1994.

TECHNICAL FIELD

The present invention relates to a detecting apparatus for detecting defects of wires on a wiring board.

BACKGROUND ART

Conventionally, a variety of voltage detecting apparatuses have been used to test for disconnection, short-circuit, and so on in a predetermined portion of an object under measurement such as an electrical circuit or the like. This type of voltage detecting apparatuses have been such that detect a voltage at a predetermined position on an object under measurement by contacting a probe at the predetermined position.

However, taking printed wiring boards as an example, a trend of enhancing the density on the printed wiring boards, i.e., finer wiring patterns, finer pitches, and an increased number of layers has been rapidly advanced, particularly in these days. While the width of wires on THD (throughhole mounted device) boards is 1.27 mm pitch, SMD (surface mounted device) boards require 0.3 mm pitch of wire width, and COB (chip on board) boards require 0.1 mm pitch of wire width. Such a trend of increasing the density of wires on printed wiring boards may result in an increase in the occurrence of defects such as disconnected and short-circuited wires. Thus, a more accurate and low cost wire testing method has become necessary in a printed wiring board testing procedure. Generally, the occurrence of defects such as disconnected and short-circuited wires increases as the number of wires increases, the wire width is reduced, and the number of layers is increased. Therefore, conduction and insulation tests for printed wiring boards and tests for narrower and wider wires have become indispensable steps in order to prevent beforehand possible troubles after the mounting of electronic devices thereon.

Currently used printed wiring board testing apparatuses may be roughly classified into two: a contact type and a non-contact type. There are two types of contact type testing apparatuses: a type which utilizes a fixture corresponding to a printed wiring board and a flying type which freely moves several probe pins on a printed wiring board for performing an electrical test. With a fixture type testing apparatus, contact probe pins having a spring are applied with a pressure so as to come into contact with lands on a printed wiring board. Then, a predetermined bias voltage is applied to detect a conduction situation between respective lands, i.e., between respective probe pins, which are compared with reference data or design data to conduct a test of wires. Since the fixture must be manufactured for each printed wiring board under test, the fixture type testing apparatus has disadvantages that designing and manufacturing of the fixture causes a cost and that fixtures are not compatible. A further disadvantage is that it cannot be used for testing printed wiring boards having a pitch equal to or less than 0.5 mm due to limits of accuracies in the shape of the probe pins and a pin upholding mechanism. The flying type is capable of testing printed wiring boards having a wiring pitch ranging from 0.5 to 0.15 mm. However, since pins must be moved to many points under detection on a printed wiring board for testing, it has disadvantages that a longer time is taken than the fixture type and that the apparatus is expensive. Moreover, since the contact-type testing apparatus cannot simultaneously obtain information on two-dimensional wires and conduction of a printed wiring board, the locations of narrower wires are difficult to detect. It is therefore necessary to use visual or optical image processing together with the contact-type testing apparatus. For this purpose, a method of utilizing an image inputted from a camera is used together.

On the other hand, non-contact type testing apparatuses include printed wiring board appearance testing apparatuses which conduct a test utilizing an image of a printed wiring board under test. The printed wiring board appearance testing apparatuses are again classified into a scheme which compares an image of an object under test with an image of a good sample, a feature extraction scheme which checks whether or not a pattern is formed in conformity to a predetermined design rule, a testing scheme which relies on a comparison with CAD data of a printed circuit board, a particular point recognition scheme, and a scheme which combines them. These schemes are capable of detecting the locations of narrower wires. However, they are not capable of detecting the locations of short-circuited wires.

As to the testing of multiple-layer printed wiring boards, since wires on inner layers of a multiple-layer printed wiring board cannot be tested after laminating the layers, the test must be conducted before adhering the inner layer plates. A voltage detector utilizing an electronic beam, which is one of non-contact type testing apparatuses, detects a voltage between wires or a voltage between a wire and a probe and tests a printed wiring board based on the detected voltage. This voltage detector can detect a voltage without bringing probes into contact with a board under test. However, in this voltage detector, a portion under measurement of the board must be placed in a vacuum, and that portion must be exposed. In addition, there is a fear that the portion under measurement be damaged by the electronic beam.

Laid-open Japanese Patent Application No. 59-500186 and Laid-open Japanese Patent Application No. 63-133068 describe testing apparatuses for integrated circuits utilizing an electro-optical crystal. These testing apparatuses utilize the nature of the electro-optical material which exhibits a double refractive index varying depending on an electrical field. Irradiation of the electro-optical material with laser light causes a change in the phase difference between vibration components in two directions orthogonal to the irradiated light, i.e., a polarized light condition depending on the magnitude of an electrical field. Generally, a change in the polarized light condition can be converted into a change in magnitude by passing the polarized light through a polarization plate set in a certain appropriate axial direction. If pulse waves are used for the laser light, a temporally changing electrical field, i.e., a temporal change in a electrical signal can be measured with a resolution corresponding to the pulse width of the laser. The electro-optical crystal used herein may be an inorganic material such as $LiNbO_3$ or the like. Since the dielectric coefficients of these inorganic materials are generally larger than the dielectric coefficient between a portion under measurement and the electro-optical crystal, an electrical field applied to the electro-optical crystal becomes smaller, thus presenting a disadvantage that the measuring sensitivity is degraded. Therefore, for improving the dielectric coefficient between a portion under measurement and the electro-optical crystal, Laid-open Japanese Patent Application No. 3-156379 proposes the insertion of an organic material such as ethyl alcohol, ethylene glycol, or the like between the portion under measurement and the electro-optical crystal, however, this has a disadvantage that the operation is practically complicated. A further disadvantage is that since light transmissible wavelengths of these inorganic electro-optical materials lie in a near infrared region, light sources usable for the detection are limited.

Laid-open Japanese Patent Application No. 1-119778, in turn, describes a non-contact type testing apparatus for testing printed wiring boards comprising a plurality of electronic components, wherein a polymer electro-optical material is utilized. However, while this testing apparatus can measure signals flowing between electronic components, it cannot detects defects such as narrower wires and short-circuited wires on a printed wiring board.

Taking a further example, liquid-crystal display panels are largely expected to have a higher image quality and so on as larger sizes and finer pitches have been progressed, so that researches have been actively advanced for practical use, and the commercialization of small-size and medium-size liquid-crystal display panels have been realized. For example, in an active matrix type liquid-crystal display panel, active elements such as transistors functioning as switching elements, diodes and so on must be formed for all pixels on a liquid-crystal display panel. Although the manufacturing process is extremely complicated, the current situation has been advanced to such an extent that active matrix type liquid-crystal display panels having more than one million pixels have been sold in the market. For the active matrix type liquid-crystal display panels having increasingly finer pitches, a reduction in the cost of the manufacturing process and an increased yield rate by improving the process are highly demanded.

As to the cost reduction, it is of particular importance that defective liquid-crystal display panels be found as early as possible. Currently, LCD panels are tested in most cases after liquid-crystal cells have been formed, so that products found as detectives must be deleted together with implanted liquid crystals. Particularly, in the case of color displays, defective liquid-crystal display panels must be deleted together with a color filter inserted therein, thus leading to an increase in the manufacturing cost. In this sense, it is extremely advantageous to conduct a test at a stage of panels before liquid-crystals are implanted.

Conventionally, an electrical measuring method and an optical measuring method have been employed for testing liquid-crystal display panels. As the electrical method, a voltage measurement test using probe pins may be given. For example, this corresponds to an apparatus which basically relies on a resistance measuring method to conduct a test exclusively for disconnection and short-circuit between respective gate lines, drain lines, and Cs buses by contacting the probe pins on external connection pads or measuring pads of a thin-film transistor (TFT) array in an active matrix type liquid-crystal display panel. However, with such an electrical measurement, it is impossible to test all pixels on an active matrix type liquid-crystal display panel having more than one million pixels. It has a disadvantage that an extremely long time would be taken even if all pixels were tested, so that it is not practical. As an optical measuring method, a liquid-crystal display panel visual sensing test may be given, which is conducted after liquid-crystals are implanted between pixel electrodes and opposite electrodes of an active matrix type liquid-crystal display panel to form cells. In this test, the surface of a liquid-crystal display panel under measurement is irradiated with light, a two-dimensional CCD sensor is utilized to read an image of the panel in place of human's eyes, adjacent periodical patterns are sequentially compared using pattern recognition and image processing techniques, and their differences are detected as defects. Since this test is basically an appearance test, it is capable of recognizing not only dust particles and foreign substances attached on the panel but also defective patterns, however, it is not capable of accurately detecting electrical disconnection and short-circuit.

In addition, there are a voltage detector utilizing an electron beam as one of non-contact type testing apparatuses, as mentioned above, and also a system for measuring secondary electron energy by a charged semi-conductor. The voltage detector can detect a voltage without bringing a probe in contact with a panel under measurement. However, a liquid-crystal display panel under measurement need be placed in a vacuum condition, and a portion subjected to the test must be exposed. Moreover, there is a fear that the liquid-crystal display panel under measurement be damaged by the electron beam.

Laid-open Japanese Patent Application No. 5-240800 and Laid-open Japanese Patent Application No. 5-256794 describe testing apparatuses for liquid-crystal display boards utilizing an electro-optical material or a polymer distributed liquid-crystal sheet.

The aforementioned testing apparatus utilizing an electro-optical material takes advantage of a property of the electro-optical material that its double refractive index varies depending on an electrical field from a liquid crystal display panel. Irradiation of an electro-optical material with laser light causes a change in the phase difference between vibration components in two directions orthogonal to the irradiated light, i.e., a polarized light condition depending on the magnitude of an electrical field. Generally, a change in the polarized light condition can be converted into a change in electrical magnitude by passing the polarized light through a polarization plate set in a certain appropriate axial direction. By observing the level of the electrical magnitude at a certain position, a liquid crystal display substrate can be tested for defects. Generally, inorganic crystals such as $LiNbO_3$ or the like are mainly used as the electro-optical material at present. These inorganic crystals have a disadvantage that an electrical field applied to an electro-optical crystal becomes smaller since the dielectric coefficients of these inorganic materials are generally larger than the dielectric coefficient between a portion under measurement and the electro-optical crystal, thus degrading the measuring sensitivity. The crystals also have a defect that, in general, either inorganic or organic, a large area cannot be fabricated.

On the other hand, a polymer distributed liquid-crystal sheet is enclosed in a transparent case and positioned above a liquid crystal. When using such a liquid-crystal sheet, since a response speed of a testing apparatus, which depends on a response speed of liquid-crystal molecules with respect to an electrical field, is on the order of milliseconds, and therefore a testing time is limited.

In addition, when an integrated circuit having a multiplicity of terminals such as LSI is mounted on a printed board or the like, a conversion connector is required to extend the terminal pitch. Moreover, since recent high-speed clock integrated circuits generate a significant amount of heat, they are often enclosed in ceramics packages which exhibits a good heat dissipation. Integrated circuit which do not need to dissipate so much heat are also enclosed in cheap plastic packages. These packages for integrated circuits also tend to have increasingly narrower terminal pitches. While 0.3 mm pitch is currently in practice, 0.1 mm pitch is also under consideration.

For testing a conventional package having 0.3 mm pitch, a dedicated fixture or a flying type prober has been used. However, the former must provide a fixture having an arrangement of pins corresponding to the arrangement and the number of electrodes of a particular package, so that it lacks the compatibility. In addition, since fine pins are expensive, the cost will cause a problem. Further, it is difficult to support fine pitches such as 0.1 mm pitch from a technical viewpoint. On the other hand, in the latter case, those sold in the market for large printed board is substituted. This method, which is different from the above-mentioned fixture method, utilizes several needle-like probes. Thus, while the testing apparatus as a whole is expensive, the probes, which are expendable supplies, are cheap. Nevertheless, since it is difficult to precisely bring the probes into contact with small electrodes, a variety of techniques are required. Moreover, since several probes must be brought into contact with electrodes, it has a disadvantage that a longer testing time is required, although exhibiting a good compatibility. Further, since the probes are formed in a fine needle shape so as to support fine electrodes, and are plated with gold on the surfaces thereof, there is another disadvantage that gold plated on electrodes be damaged during a test.

The testing methods using mechanical contact as described above have a certain limit, and present difficulties in manufacturing fixtures and pin probes corresponding to packages having pitches of 0.1 mm or less and in making measurements using them.

In view of the problems mentioned above, it is a first object of the present invention to provide a detecting apparatus for detecting defects of wires on a wiring board which is capable of supporting wires having narrow widths and of detecting narrower wires, conduction conditions of wires, and locations of short-circuited wires in a non-contact manner.

It is a second object of the present invention to provide a detecting apparatus for detecting defects on a wiring board of a printed wiring board.

It is a third object of the present invention to provide a detecting apparatus for detecting defects of wires on a printed wiring board which is capable of detecting defects of not only wires on the top surface and rear surface but also on internal layers in a non-contact manner.

It is a fourth object of the present invention to provide a detecting apparatus which achieves a high detecting accuracy, supports small pixel areas, and detects disconnected, narrower, and short-circuited wires, and so on of transparent electrodes on a liquid crystal display panel in a non-contact manner, prior to assembling liquid-crystal cells without damaging the liquid-crystal panel.

It is a fifth object of the present invention to provide an apparatus for finding defects of wires which is capable of supporting fine pitches of packages for integrated circuits.

DISCLOSURE OF THE INVENTION

According to the present invention, there is provided a detecting apparatus for detecting defects of wires on a wiring board comprising at least one layer of wires. The detecting apparatus comprises:

an optical sensor including a transparent substrate, a transparent electrode disposed on the transparent electrode, a film of a polymer non-linear optical material disposed on the transparent electrode, and a reflective film disposed on the film, and positioned close to a wire to be measured on the wiring board and without contacting same;

a sensor head including a light source, optical means for guiding light from the light source into the optical sensor, and detecting means for detecting reflected light from the optical sensor to derive a signal corresponding to the intensity of the reflected light when the wire is applied with a voltage; and a processing unit for processing the signal derived from the detecting means to output a signal corresponding to the presence or absence of a defect on said wire. Here, the defects of wires mean narrower or disconnected wires, short-circuit between the wires, or any arbitrary combination thereof.

The detecting apparatus configured in this way according to the present invention utilizes an electro-optical effect to detect defects of wires. In known techniques utilizing the electro-optical effect, for example, a detecting apparatus disclosed in Laid-open Japanese Patent Application No. 1-119778 is a so-called in-circuit board tester which is intended to measure signals between electronic parts mounted on a printed wiring board, whereas, the detecting apparatus of the present invention aims at detecting defects of wires before electronic parts are mounted. Also, the detecting means is moved over a board under test to scan same, thereby detecting defects of wires. In this respect, the detecting apparatus of the present invention differs from the apparatus disclosed in the Laid-open Japanese Patent Application No. 1-119778 which only scans light beams by a mirror.

In the detecting apparatus of the present invention, the optical sensor and the head sensor may be integrated or separated. In the latter case, the optical sensor is previously fixed above a wiring board so as not to contact the wiring board, and the sensor head is moved over the fixed optical sensor for scanning the wiring board.

In the detecting apparatus of the present invention, the optical sensor may be formed in a size substantially identical to or larger than a wiring board under test. In this way, the sensor head is moved, with the optical sensor remaining fixed, so as to form a configuration for scanning the wiring board with beam-like light therefrom. By arranging the optical means and the detecting means in a linear shape and using linear light in place of beam-like light, a measuring time can be reduced. Alternatively, by arranging the optical means and the detecting means in a planar shape and using planar light in place of beam-like light, the measuring time can also be reduced.

The detecting apparatus of the present invention can also be used to detect defects of wires on a printed wiring board having at least one layer of wires. The printed wiring board may be a printed wiring board having one layer of wires or a multiple-layer printed wiring board. For detecting defects of wires in the multiple-layer wiring board, it is possible to detect defects of wires on all layers by one operation as well as to detect defects of wires on each layer. The material of the printed wiring board is not particularly limited, and a measurement can be made with the detecting apparatus of the present invention as long as the material is commonly used as a printed wiring board.

The detecting apparatus of the present invention can also be used to test a liquid-crystal display panel comprising a transparent glass substrate having a transparent electrode. As this type of liquid-crystal display panels, there are a simple matrix type liquid-crystal display panel represented by STN and an active matrix type liquid-crystal display panel having active elements (transistors such as thin-film transistors and bulk transistors, and diodes such as metal-insulator-metal diodes, ZnO varistors, metal semi-insulator diodes, and ring diodes). The present invention is capable of simultaneously detecting disconnected wires, narrower portions, and short-circuit which are defects of transparent electrodes in both of them. The transparent electrode in the present invention means scan electrodes in the simple matrix type liquid-crystal display panel and scan electrodes, signal electrodes and active elements in the active matrix type liquid-crystal display panel. These transparent electrodes are not limited in shape, and defects of wires can be detected by the detecting apparatus of the present invention even if the liquid-crystal display panel is coated with an orientation film.

The detecting apparatus of the present invention can also be used to detect defects in packages for integrated circuits. As such packages, there may be given ceramic-Ball Grid Array (c-BGA), plastic Ball Grid Array (p-GBA), Qaud Flat Package with Bumper (BQFP), Butt Joint Pin Grid Array (BJPGA), Cerdip, Cerquad, Ceramic Leaded Chip Carrier (CLCC), Plastic Leaded Chip Carrier (PLCC), Dual Flat Package (DFP), ceramic-Dual In-line Package (c-DIP), plastic-Dual In-line Package (p-DIP), Small Out-line Package (SOP), Dual Tape Carrier Package (DTCP), Quad Flat Package (QFP), Fine pitch Quad Flat Package (FQFP), Quad Flat Packagewith Guard ring (GQFP), ceramic Pin Grid Array (c-PGA), plastic Pin Grid Array (p-PGA), Leadless Chip Carrier (LCC), Land Grid Array (LGA), Low profil Quad Flat Package (LQFP), L-QUAD, Multi-Chip Module (MCM), Metric Quad Flat Package (MQFP), ceramic Quad Flat Package (c-QFP), plastic Quad Flat Package (p-QFP), Metal Quad (MQUAD), Mini Square Package (MSP), Piggy Back, Quad Flat High Package (QFH), Quad Flat I-leaded Package (QFI), Quad Flat J-leaded Package (QFJ), Quad Flat non-leaded Package (QFN), Tape Carrier Package (TCP), Quad Tape Carrier Package (QTCP), Quad In-line Package (QUIP), Shrink Dual In-line Package (SDIP), Single In-line Package (SIP), Single In-line Memory Module (SIMM), Skinny Dual In-line Package (Skinny-DIP), Slim Dual In-line Package (SL-DIP), Small Out-line Package (SOP), Small Out-line I-leaded Package (SOI), Small Out-line J-leaded Package (SOJ), Small Out-line L-leaded Package (SOL), Small Out-line Non-fin (SONF), Small Out-line Package Wide-type Shrink Quad Flat Package (SQFP), Shrink Single In-line Package (SSOP), Surface Vertical Package (SVP), Shrink Zigzag In-line Package (SZPI), Thin-Srink Small Outline Package (Thin-SSOP), Test Pad QFP (TPQFP), Thin Quad Flat Package (TQFP), Thin Small Out-line Package (TSOP), Ultra Small Outline Package (TSOP), Ultra Thin SmallOutline Package (UTSOP), Zigzag In-line Package (ZIP), Very short pitch Small Out-line Package with Heat sink (VHSO), Very Small Quad Flat Package (VQFP), Very Short Pitch Small Out-line Package (VSO), Very Small Out-line Package (VSOP), and so on.

The optical sensor is positioned close to but without contacting the package for an integrated circuit so as to overlay an entire portion thereof bonded to an integrated circuit. The electrodes are applied with a voltage from the pin side in order to detect defects of electrodes in the package for an integrated circuit by the principles as mentioned above. The detecting apparatus of the present invention can also be used to test packages after coated with solder resist.

BEST MODE FOR IMPLEMENTING THE INVENTION

FIGS. 1(a)–(d) illustrate steps of manufacturing an optical sensor used for a detecting apparatus according to the present invention. First, a transparent electrode 12 is disposed on a transparent substrate 10 (FIG. 1(a)). The transparent substrate 10 must be transparent in a range of wavelengths of incident light, and a group of glasses such as soda glass, quartz glass and pyrex glass or a group of optical plastics are suitable. In the present invention, it is desirable to utilize $\gamma_{33}$ which guides incident light to obliquely impinge on a thin film of a polymer non-linear optical material and is a maximum non-linear effective component of the material, when detecting defects of wires on a wiring board. However, obliquely impinging incident light disadvantageously degrades the beam profile. To solve this problem, the thickness of the transparent substrate 10 must be as small as possible. For example, when the diameter of incident light is converged to 10 μm or less, the thickness of the transparent substrate is desirably about 1000 μm or less. More preferably, the thickness ranges approximately from 300 to 400 μm in consideration of the ease of handling.

The transparent electrode 12 must be transparent in a wavelength range of incident light. As the transparent electrode 12, inorganic conductive materials such as ITO (Indium-Tin-Oxide), $SnO_2$, or the like may be used. The film thickness of the transparent electrode 12 is preferably small in order to reduce the reflectivity of the incident light on the transparent electrode 12. Preferably, the thickness of the transparent electrode 12 ranges approximately from 100 to 1000 angstroms. A method of disposing the transparent electrode 12 on the transparent substrate 10 is not particularly limited, and any of conventionally known methods may be used. For example, a vacuum vapor deposition method may be used. Alternatively, a commercially available Nesa glass (a registered trade mark) or the like may also be used.

Figure 1:
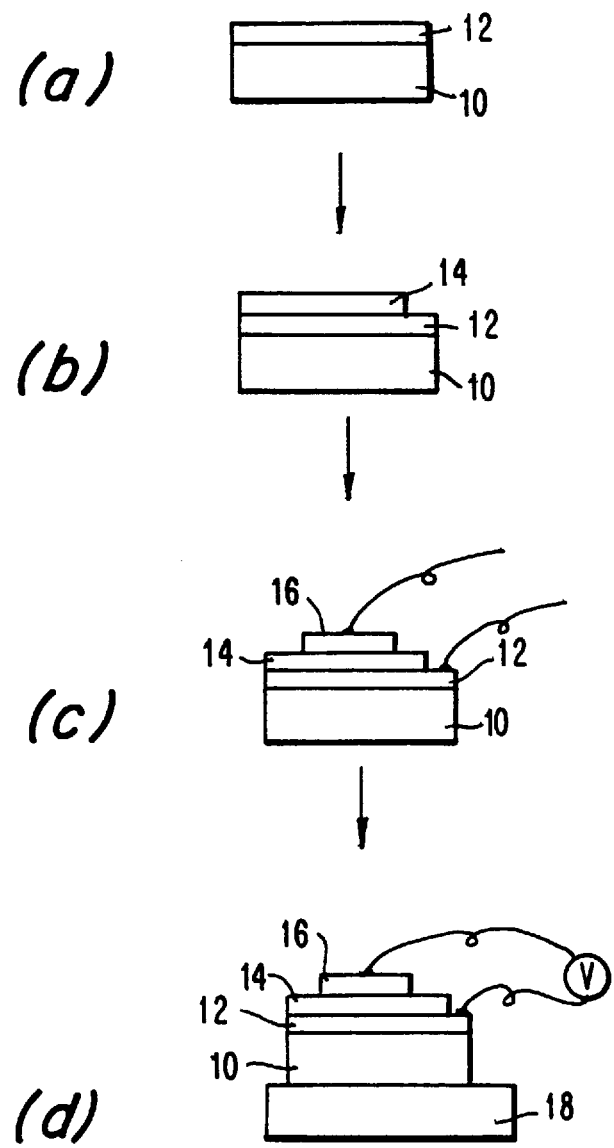
FIGS. 1(a)–(d) are diagrams orderly illustrating steps of manufacturing an optical sensor for a detecting apparatus according to the present invention.

A thin film 14 of a polymer non-linear optical material is disposed on the transparent electrode 12 (FIG. 1(b)). For the thin film 14, a conventionally known arbitrary thin film forming method may be used. For example, the polymer non-linear optical material is dissolved in a solvent such as cyclohexanon, and the solution is spin-coated on the transparent electrode 12 at a rotational speed of approximately 200–5000 rpm. Next, the solution is heated to evaporate or remove the solvent, thus forming the thin film 14 of the polymer non-linear optical material. The thin film 14 must have a thickness which can sufficiently take in an electrical field generated from wires on a wiring board. When measuring an electrical field between a wire on a wiring board and the transparent electrode, or an electrode arbitrarily generated from a wire on a wiring board, if the dielectric coefficient between the optical sensor and the wire is smaller than the dielectric coefficient of the polymer non-linear optical material, the thickness is preferably in a range of approximately 10–1000 μm which is sufficiently larger than the distance between the optical sensor and the wire on the printed wiring board. More preferably, the thickness is approximately 20 μm.

It is desirable that a group of atoms having non-linear optical activity in the polymer non-linear optical material (also referred to as "chromophore") be oriented in a fixed direction in the thin film 14. This is because a larger non-linear optical effect is obtained by orienting the group of atoms. The direction of the orientation may be in a direction parallel with the surface of the thin film 14 or in a direction perpendicular to the surface of the thin film 14. Alternatively, the orientation may be oblique to the surface of the thin film 14. For orientation processing, the following method may be used by way of example.

First, as illustrated in FIG. 1(c), an electrode 16 for orientation is disposed on the thin film 14 for the orientation processing. The electrode 16 for orientation may be disposed over a whole surface of the thin film 14 or only on a portion subjected to the orientation processing. A material for the electrode 16 for orientation preferably has a small resistance value, and gold, silver, copper or aluminum, for example, may be used. Preferably, the film thickness of the electrode 16 for orientation is approximately 600 angstroms or more, and approximately 1000–1500 angstroms is particularly desirable. For disposing the electrode 16 for orientation, a vacuum vapor deposition method may be used by way of example. For fixing leads for connecting a power supply to the electrode 16 for orientation and the transparent electrode 12 on the electrode 16 for orientation and the transparent electrode 12, an electrically conductive adhesive may be used.

Next, as illustrated in FIG. 1(d), a hot plate 18 is used to heat the thin film 14 to a temperature equal to or higher than its glass-transition temperature. While there is not a particular upper limit to the heating temperature, it is practical to choose a temperature equal to or lower than the melting point where the thin film 14 can maintain its shape. After the thin film 14 is sufficiently heated to give mobility to the group of atoms having the non-linearity optical activity, a voltage is applied between the electrode 16 for orientation on the thin film 14 and the transparent electrode 12. For producing a larger non-linear optical effect, the applied voltage should be as high as possible, and an applied time should be sufficiently long to complete the orientation of the group of atoms under the application of the voltage. The applied voltage is preferably in the range of approximately 100–300 V/μm, as long as it does not cause the thin film 14 to break down, and the applied time is preferably several minutes. Subsequently, the thin film 14 is cooled to a room temperature while the thin film 14 is continuously being applied with the voltage to fix the orientation of the group of atoms. With the processing as described above, the group of atoms can be oriented in a direction perpendicular to or in a direction oblique to the surface of the thin film 14.

The electrode for orientation on the thin film used for the orientation processing is generally removed with an etchant after it is used as an electrode for measuring the electro-optical constant of the thin film, later described, and as a reflective film. A reflective film is disposed on the thin film from which the electrode for orientation was removed with the etchant. As the reflective film, a metal mirror, or a multiple-layer mirror made of dielectric materials may be used. As the multiple-layer mirror of dielectric materials, a mirror formed of, for example, alternately laminated thin films of $SiO_2$ and thin films of $TiO_2$ may be used. For the lamination, a vacuum vapor deposition method may be used. The optical sensor thus created is diced in conformity to the shape of a wiring board.

While inorganic materials and organic low-molecular materials are known, in addition to polymer materials, as polymer non-linear optical materials used for the optical sensor of the present invention, the present invention preferably employs a polymer non-linear optical material in view of difficulties in producing a highly sensitive and large-sized film with an inorganic material or an organic low-molecular material.

As a polymer non-linear optical material used in the present invention, it is preferable to use a polymer material having a second-order non-linear optical effect, a small dielectric coefficient, a large electro-optical constant, and a high transparency. For example, the present invention may employ polymer materials expressed by the following general formula I and general formula II:

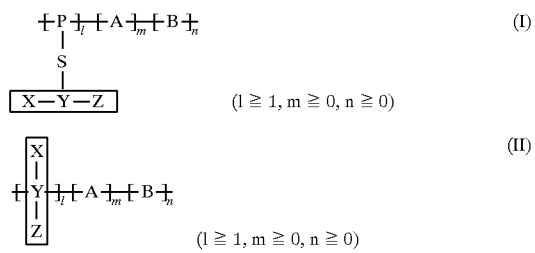

In the general formula I, P is a main chain of a non-linear optical active copolymer. As P, a polyvinyl system, a polysiloxane system, polyoxyalkylene system, a NRpolyvinylidene system, a polyurethan system, a polytriazine system, a polyester system, or a polyamide system is preferable. S is a spacer group comprising a direct coupling or a straight-chain hydrocarbon radical having a number of carbon atoms ranging from 1 to 20. Since the spacer group is abundant in flexibility, chromophores coupled to ends of the spacer group are provided with larger mobility. [X—Y—Z] is a chromophore having a non-linear optical activity, wherein X is an electron donor radical, and for example, —NR$_1$—, —O—, or —S— is preferable. Incidentally, as R$_1$, hydrogen or a lower alkyl radical such as a methyl radical may be used. Y is a π-electron conjugated system, and for example, a stilbene system, an azobenzene system, a biphenyl system, diphenylbutadiene system, or a disianovinyl-hexatriene system is preferable. Z is an electron acceptor radical, and for example, —NO$_2$, —CN, or —CF$_3$ are preferable.

Further, A is a copolymer unit which has no non-linear optical activity, and B is a copolymer unit and/or a functional copolymer unit having another function. Also, chemical coupling forms of a spacer group and a chromophore include, for example, the followings;

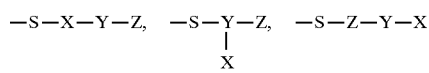

In the general formula II, [X—Y—Z], which is a chromophore having a non-linear optical activity, constitutes a main-chain unit of a non-linear optical active copolymer. The definition of Y, Y, Z, A and B is similar to those of the foregoing general formula I. Also, chemical coupling forms of the chromophore may include, for example, the followings:

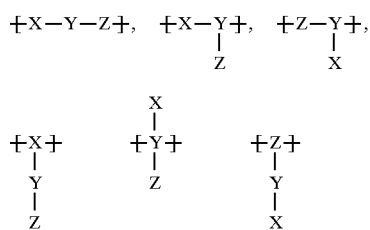

As specific polymer non-linear optical materials, those described, for example, in U.S. Pat. Nos. 4,801,670, 5,415, 510, 5,155,195, 5,171,803, 4,694,066, 4,795,644, 4,822,865, 4,810,338, 4,835,235, 4,851,502, 4,865,430, 4,867,540, 4,913,844, 4,915,491, 4,962,160, 4,757,130, 4,808,322, 4,978,476, 5,002,361, 5,041,509, 5,044,725, and 5,061,760 may be used.

Particularly preferably, a methacrylated copolymer pendent with nitroaminostilbene or indolynilazobenzene, expressed by the following formula III and formula IV, may be used as a polymer non-linear optical material.

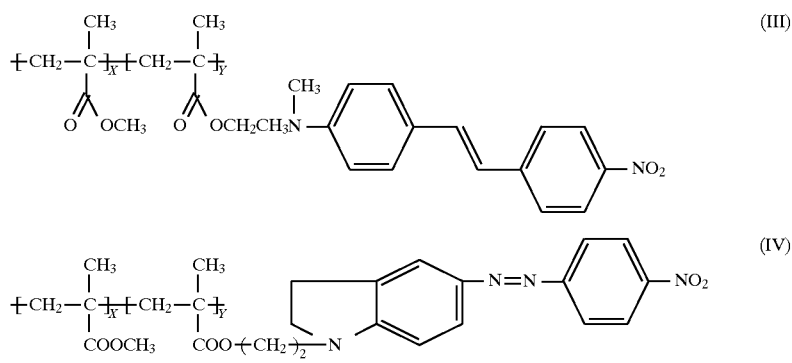

In addition, a polymer including a triazine ring comprising a repetition unit expressed by the following formula V is also preferable as a polymer non-linear material. With a polymer including this kind of triazine ring, the formation of a high quality film is possible, so that a more heat resistant material is expected.

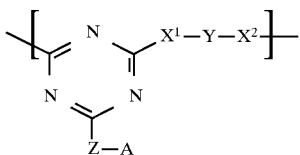

where $X^1$ and $X^2$ are S, $NR^1$ or O which may be identical or different;

$R^1$ is a hydrogen atom, an alkyl radical or an aryl radical;

Y is an alkylene radical, a bivalent substituted or non-substituted aromatic ring radical including no pigment molecular residue, a bonded or condensated aromatic ring radical, or a radical expressed by:

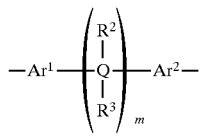

$Ar^1$ and $Ar^2$ are bivalent substituted or non-substituted aromatic radical which may be identical or different;

$R^2$ and $R^3$ are a hydrogen atom or an alkyl radical which may be identical or different;

Q is a carbon atom or a silicon atom;

m is an integer from 1 to 4;

z is a spacer group comprising a radical expressed by —G—$(CH_2)$n— (where n is an integer from 1 to 10) or a direct coupling;

G is S, $NR^4$, or O;

$R^4$ is a hydrogen atom, an alkyl radical, or an aryl radical; and

A is an organic pigment molecule residue in which an electron donative group and an electron attractive group are conjugated through a π-electron system. A mean weight molecular amount of this polymer is generally in a range of approximately 5,000 to approximately 1,000,000. Particularly preferably, copolymers expressed by the following formula VI and formula VII may be used as polymer non-linear optical materials:

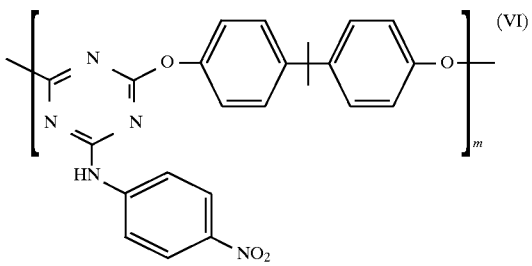

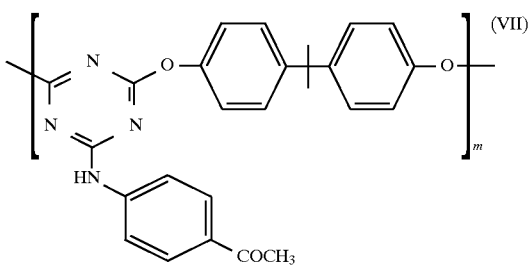

Since such polymer non-linear optical materials exhibit smaller dielectric coefficients as compared with nonorganic electro-optical crystals and are capable of efficiently taking in a voltage applied to wires even if they are placed in a close approximation to an object under measurement, a measuring sensitivity can be improved. In addition, since these polymer non-linear optical materials have extremely high response speeds to an electrical field, i.e., on the order of picosecond or higher, they are suitable for high speed measurements.

Figure 2:
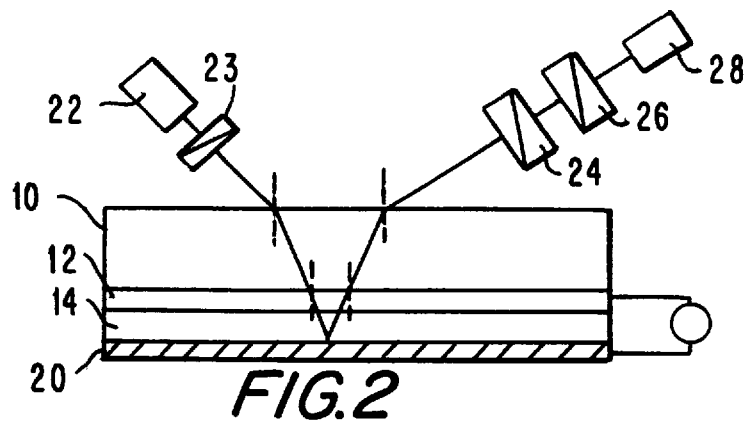
FIG. 2 is a diagram for explaining how an electro-optical constant of the optical sensor of FIG. 1 is measured.

A polymer non-linear optical material having a group of non-linear optical active atoms oriented in a direction not parallel with the surface of the thin film, as mentioned above, has a double refractive index which varies most sensitively in response to a change in electrical field in a direction parallel with the orientation direction thereof. FIG. 2 illustrates a measuring apparatus for deriving an electro-optical constant of an optical sensor having a group of non-linear optical active atoms oriented in a direction perpendicular to the surface of the thin film 14. In FIG. 2, reference numeral 10 designates a transparent substrate, 12 a transparent electrode, 14 a thin film of a polymer non-linear optical material, and 20 a reflective film which also functions as an electrode. Light from a light source 22, which is transformed into linear polarized light by a polarizer 23, is incident to the optical sensor from the transparent substrate 10 side, passes through the thin film 14, and is reflected by the reflective film 20. The reflected light is detected by a photoelectric transducer 28 through a Babinet-soleil compensator 24 and an analyzer 26. A modulation voltage is applied between the transparent electrode 12 and the thin film 14 from an external power supply, and the double refractive index of the polymer non-linear optical material also varies depending on the modulation voltage, so that the intensity of the reflected light detected by the photoelectric transducer 28 also varies. Refer to, for example, C. C. Teng and H. T. Man, Appl. Phys. Lett. 56(18), 30 Apr. 1990 for details of the measuring method. For example, when a light source 30 at 830 nm was used, $γ_{33}$ equal to or more than 30 pm/V was obtained from the photoelectric transducer 28. Incidentally, the transparent electrode 12 of the optical sensor 100 is used as a ground when the modulation voltage is applied, and is diced in conformity to the shape of a board under test.

Figure 3:
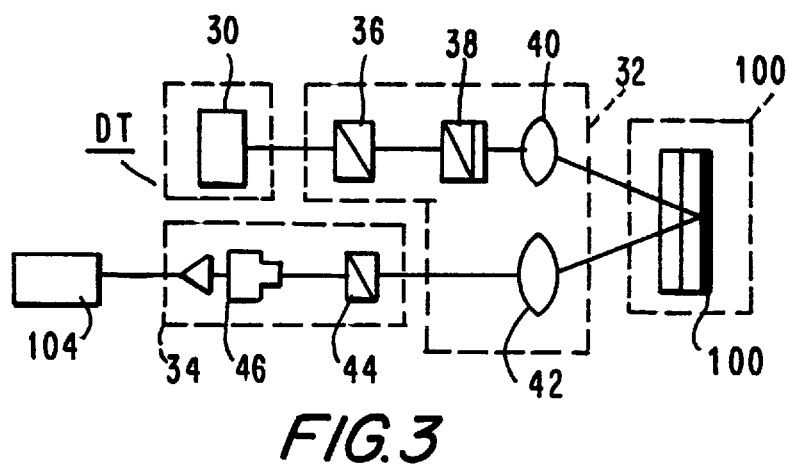
FIG. 3 is a diagram schematically illustrating the configuration of an embodiment of the detecting apparatus according to the present invention.

FIG. 3 is a diagram schematically illustrating the configuration of an embodiment of the detecting apparatus according to the present invention. Specifically, the detecting apparatus of the present invention comprises an optical sensor 100 including a thin film of the above-mentioned polymer non-linear optical material, a sensor head 102, and a signal processing unit 104, wherein the sensor head 102 has a light source 30, an optical means 32 for guiding light from the light source 30 into the optical sensor 100, and a detecting means 34 for detecting the light incident to the optical sensor 100 after reflected from a reflective film of the optical sensor 100.

As the light source 30, off-the-shelf semiconductor lasers capable of outputting wavelengths ranging from 600 to 1550 nm, gaseous lasers such as He—Ne laser, solid-state lasers such as YAG and $YVO_4$, lasers which oscillate second harmonics, and so on may be used. The light source 30 may be in a one-dimensional linear shape or in a two-dimensional planar shape. The optical means 32 for guiding light from the light source 30 into the optical sensor 100 has, for example, a polarizer 36 for selecting a predetermined polarized light component from the light from the light source 30, a λ/4 wavelength plate 38 for optically applying a bias equivalent to an electrical bias, a first optical member 40 for guiding light into the optical sensor 100 at an appropriate angle, and a second optical member 42 for guiding reflected light from the optical sensor 100 into the detecting means 34. When the light source 30 is arranged in a linear shape or in a planar shape, the optical means 32 can be also arranged in a linear shape or in a planar shape corresponding thereto. As the optical members 40, 42, for example, optical lenses, optical mirrors, prisms, and optical fibers may be used.

The detecting means 34 for detecting reflected light from the optical sensor 100 comprises an analyzer 44 set at an angle so as to pass therethrough a polarized light component perpendicular to or a polarized light component parallel with a polarized light component passing through the polarizer 36, and a photoelectric transducer 46 such as a photodiode and an optical electron duplicating tube. An electrical signal from the photoelectric transducer 46 is processed by the signal processing unit 104 such as a computer or the like. When the light source 30 is arranged in a linear shape or in a planar shape, the detecting means 34 is also arranged in a linear shape or in a planar shape corresponding thereto. A linear detecting means may be composed of a combination of a linear analyzer and an array of photodiodes.

For detecting defects of wires on a wiring board, the optical sensor 100 is positioned with its reflective film 20 side close to but not contacted with a wire to be measured on the wiring board. The wire is applied with an AC voltage or a DC voltage. When the wire is applied with an AC voltage, an arbitrary voltage at frequency ranging from 1 Hz to a Terahertz band may be used, however, a frequency ranging from 100 Hz to a gigahertz band is preferable from a viewpoint of the ease of measurement. In the detecting apparatus of the present invention, the sensor head 102 or a wiring board is moved by means of a transfer means to scan the wiring board with light from the optical means 32, so that vibration noise may be introduced. Since the vibration noise exists in a range of 1 Hz–50 KHz, it is preferable that the AC voltage applied to the wire is selected within 50 kHz–100 kHz, and in addition, the noise is removed by a bandpass filter.

Light from the light source 30 is incident to the optical sensor 100 from the transparent substrate 10 side. An incident angle is in a range from approximately 1 degree to 57 degrees, and preferably from approximately 20 degrees to 45 degrees. The light incident to the optical sensor 100 passes through the thin film 14 of the polymer non-linear optical material and reflected by the reflective film 20. Since the double refractive index of the thin film 14 varies depending on an electrical field generated by the voltage applied to the wire, the plane of polarization of the light passing through the thin film 14 varies in response to a variation in the refractive index. As a result, as the plane of polarization of the incident light differs from that of the exiting light, the intensity of light passing through the analyzer 44 changes depending on the direction of the plane of polarization. This change in the intensity is transduced into an electrical signal by the photoelectric transducer 46. In this case, the transparent electrode 12 in the optical sensor 100 is preferably at a ground potential.

In the detecting apparatus DT of the present invention, the optical sensor 100 and the sensor head 102 may be integrated or separated. The optical sensor 100 and the sensor head 102, when integrated, or the sensor head 102, when separated, is moved by a plane transfer means (not shown) on a wire on the wiring board in a non-contact manner. In this way, the wiring board is scanned. The plane transfer means may be implemented by a well known means and generally has a moving accuracy of ±30 $\mu$m or less in repetition. When a light converging system such as a lens is used as the first optical means 40, the beam diameter can be changed to approximately 1 $\mu$m to 5 mm by the optical member 40. Since the beam diameter of light corresponds to the detecting accuracy of the apparatus, the detecting apparatus DT of the present invention consequently has the detecting accuracy of approximately 1 $\mu$m to 5 mm.

In this way, a combined use of a plane transfer means and a light converging system makes it possible to not only detect defects of wires, corresponding to all of a detection pitch of 1.27 mm required by THD boards, a 0.3 mm pitch required by SMD boards, and a 0.1 mm pitch required by COB's, but also detect defects of transparent electrodes having 50–100 $\mu$m unit pitches, required by fine-pitch liquid-crystal display panels, and can also be applied to packages for integrated circuits having 0.3 and 0.1 mm pitches.

When the sensor head 102 is moved by the plane transfer means to observe a voltage applied to a wire at an arbitrary location on a wiring board, the voltage applied to the wire is an AC or DC voltage ranging from approximately 1 V to approximately 1 kV. When a defect-free wiring board is scanned by light from the sensor head 102, an electrical field is applied to the thin film 14 of the polymer non-linear optical material in a portion in which wires exist, and the double refractive index of the thin film 14 of the polymer non-linear optical material varies depending on the electrical field, causing a voltage generated by the photoelectric transducer 46 to change depending on the changing amount. On the other hand, since no electrical field is generated in a portion in which no wires exist, the double refractive index of the thin film 14 of the polymer non-linear optical material does not vary, and as a result, the voltage generated by the photoelectric transducer 46 does not change either. A distribution situation of voltages detected by the detecting means 34 is displayed on an image processing/display means (not shown) of the signal processing unit 104 such as a computer or the like for each location which was scanned by the sensor head 102. In this way, it is possible to detect the presence or absence of defects of wires, i.e., narrower wires, disconnected wires, short-circuit between wires, or any arbitrary combination of them.

Figure 4:
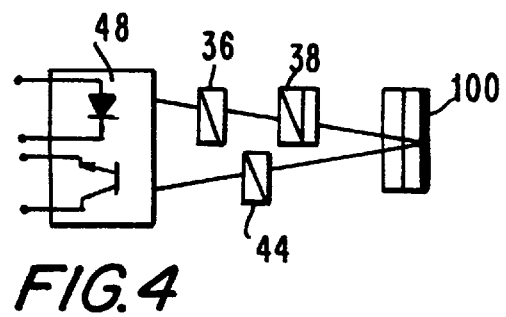
FIG. 4 is a diagram illustrating the configuration of a modified example of the detecting apparatus according to the present invention.

As illustrated in FIG. 4, an integrated device 48 having the light source 30 and the photoelectric transducer 46 integrated therein may be used in the sensor head 102. As such the integrated device 48, there are, for example, devices having integrated light emitting diodes and phototransistors, which are sold in the market under trade names of photo-reflector and photo-sensor.

The detecting apparatus DT of the present invention can also be used to simultaneously measure wires on all layers in a multiple-layer printed wiring board. In this case, voltages measured by the detecting means 34 are related both to the distances between the optical sensor 100 and wires and to the dielectric coefficient between the optical sensor 100 and the wires. More specifically, even if the same voltage is applied to each of the layers, the value of a measured voltage becomes lower as a wire is further away from the optical sensor 100 or as the dielectric coefficient between the optical sensor 100 and the wire is lower. It is therefore possible to simultaneously measure states of wires distinctively for the respective layers.

Further, the detecting apparatus DT of the present invention may be used to detect defects on an active-matrix type liquid-crystal display panel using TFT's as active elements. For detecting short-circuit between a source and a drain, only signal electrodes of the active-matrix type liquid-crystal display panel are applied with a voltage. If any of TFT's is short-circuited between a source and a drain, the voltage is applied also to a pixel electrode through the drain, whereby a signal is observed at the pixel electrode connected to the short-circuited TFT. For detecting short-circuit between a gate and a drain, scan electrodes are applied with a voltage. If short-circuit occurs between a gate and a drain, a pixel electrode is also applied with the voltage through the drain, so that a signal is observed at the pixel electrode connected to the TFT which is short-circuited between the gate and the drain.

Also, when a voltage is applied between a signal electrode and a scan electrode such that a TFT is turned on, if short-circuit occurs between a source and a gate or at an intersection of the signal electrode and the scan electrode, a normal voltage is not applied to the pixel electrode, whereby no normal signal is observed on a short-circuited pixel electrode.

For detecting disconnection of a signal electrode on an active-matrix type liquid-crystal display panel, a voltage is applied between a signal electrode and a scan electrode. If a signal electrode is disconnected, the voltage is not applied to a pixel electrode beyond the disconnected location, whereby no signal is observed on the pixel electrode. Similarly, for detecting disconnection of a scan electrode, a voltage is applied between a signal electrode and a scan electrode. If a scan electrode is disconnected, the voltage is not applied to a pixel electrode beyond the disconnected location, whereby no signal is observed on the pixel electrode.

On the other hand, for detecting defects of wires in a package for an integrated circuit, the detecting apparatus DT having the integrated optical sensor 100 and sensor head 102 is previously moved over wires close to but not contacting them, or the optical sensor 100 is previously fixed over wires close to but not contacting them, and the sensor head 102 only is moved to scan the wires.

Also, for detecting disconnected wires in a package for an integrated circuit, a voltage is applied to all wires in the package for an integrated circuit through all shorting bars if pins have not been brazed, or through a socket for voltage application if they have been brazed. Then, the package for an integrated circuit is scanned by the detecting apparatus DT to detect voltages on wires, as described above, thus detecting disconnected locations.

For detecting short-circuited wires in a package for an integrated circuit, a socket for voltage application is connected to pins of the package for an integrated circuit, and a voltage is applied to a single wire. Then, the detecting apparatus DT is used to confirm the presence or absence of wires from which a voltage is detected. If a voltage is detected from a wire other than the wire to which the voltage has been applied, these wires are short-circuited. By executing such a procedure for all wires, all the wires can be tested for the presence or absence of short-circuit. In this event, the socket for voltage application may be connected to a scanner such that a voltage is sequentially applied to wires.

Now, a process of manufacturing the optical sensor 100, which has already been described with reference to FIGS. 1(a)–(d), and the configuration thereof will be specifically explained. The aforementioned polymer non-linear optical material expressed by the formula III having methyl methacrylate and chromophores in the ratio of 50:50 mole percents is dissolved in cyclohexanon. The solution is stirred in a nitrogen atmosphere at 60° C. for 24 hours, then cooled to a room temperature, and filtrated under reduced pressure with a 0.2 $\mu$m filter to obtain a solvent of 15 weight percents. Meanwhile, ITO, which is an inorganic conductive material, is vapor-deposited on borrosillicate glass (transparent substrate 10) of 50×50×0.4 mm to form a transparent electrode 12. The transparent electrode 12 has a thickness of 185 angstroms and a resistance value of 450 $\Omega/cm^2$. Next, the transparent substrate 10 of glass having the transparent electrode 12 formed thereon is washed in pure water and is coated with the above-mentioned solution on the transparent electrode 12 by a spin coating method. When cyclohexanon is evaporated or removed by a drying operation at 160° C. for five hours, a thin film 14 is formed. When the thickness of the obtained thin film 14 was measured with a probe film thickness meter, it was 15 $\mu$m. Next, a gold electrode 16 for orientation is disposed on the thin film 14 using an ordinary vapor deposition apparatus. The electrode 16 for orientation has a thickness of approximately 1000 angstroms and a diameter of 5 mm. Wires are connected to the electrode 16 for orientation and to the transparent electrode 12 with silver paste.

Next, a hot plate 18 is used to heat the thin film 14 to a temperature equal to or higher than its glass transition temperature, i.e., 140° C. After giving mobility to chromophores having a non-linear optical activity by heating, a DC voltage of 150 V/$\mu$m is applied between the electrode 16 for orientation and the transparent electrode 12 for five minutes. The thin film 14, with the voltage continuously applied thereto, is cooled to a room temperature to fix the orientation of the chromophores.

When the thin film 14 of the optical sensor 100 thus constructed was applied with a modulation voltage at 100 V from the outside, as in FIG. 2, to observe an output of the photoelectric transducer 28, an AC component of 1.5 mV was obtained for a DC voltage component of 105 mV, and $\gamma_{33}$ was 31 pm/V, thus confirming that a voltage applied to wires on a wiring board could be measured.

Afterward, the electrode 16 for orientation is removed by etching, $SiO_2$ and $TiO_2$ are alternately vapor-deposited on the thin film 14 to provide a reflective film 20 having a thickness of approximately 1.8 $\mu$m. A reflectivity when light having a wavelength of 830 nm was incident to the reflective film 20 at an incident angle of 45 degrees was 80%.

Figure 5:
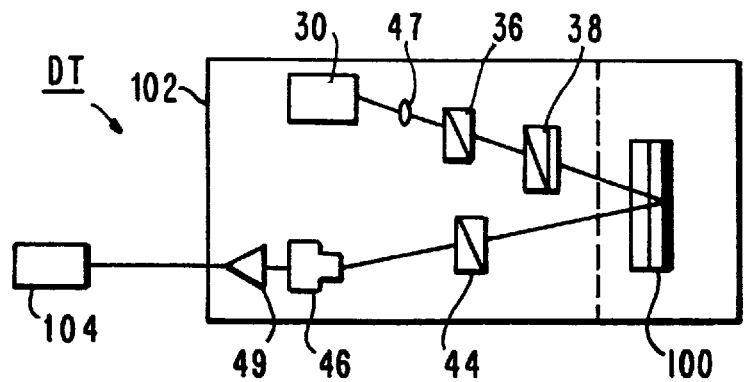
FIG. 5 is a diagram illustrating the configuration of another embodiment of the detecting apparatus according to the present invention which has an optical sensor and a sensor head in FIG. 3 integrated with each other.

FIG. 5 illustrates the configuration of another embodiment of the detecting apparatus DT according to the present invention, wherein the sensor 100 and the sensor head 102 manufactured by the steps illustrated in FIGS. 1(a)–(d) are integrated. In the sensor head 102 of this embodiment, first and second optical members 40, 42 are omitted, and a light source 30 is a semiconductor laser which generates laser light having a wavelength of 830 nm. A beam shape of the laser light from the light source 30 is reshaped by a collimator lens 47, and the reshaped laser light is transformed into linear polarized light by a polarizer 36. A $\lambda/4$ wavelength plate 38 is made of mica, and a photoelectric transducer 46 is a photodiode. The laser light emitted from the light source 30 has a beam diameter of 50 $\mu$m, and is incident to the optical sensor 100 at an incident angle of 45 degrees. The polarizer 36 has an extinction ratio of $10^{-4}$. The analyzer 44 may be of the same type as the polarizer 36. The output of the photoelectric transducer 46 is subjected to impedance conversion and pre-amplification by an operational amplifier 49, and then supplied to a signal processing system 104 for appropriate processing. Incidentally, the detecting apparatus DT of the present invention similarly functions even if the optical sensor 100 and the sensor head 102 are separated.

In the following, several application examples for detecting defects on different wiring boards using the detecting apparatus DT according to the present invention will be described in detail.

APPLICATION EXAMPLE 1

Figure 6:
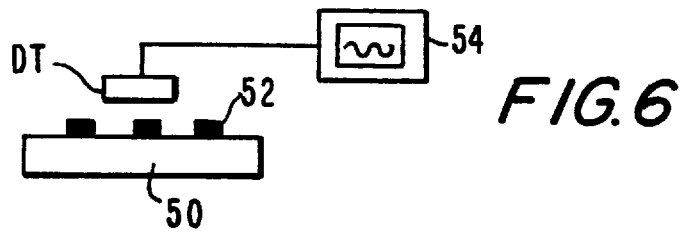
FIG. 6 is a diagram illustrating an arrangement of the detecting apparatus of the present invention when applied to detecting defects on a printed wiring board.

For detecting defects of wires on a printed wiring board using the detecting apparatus DT of FIG. 5, the detecting apparatus DT was positioned such that the sensor 100 was in close approximation to a printed wiring board 50 but without contacting the same, as illustrated in FIG. 6, and a wire 52 having a width of 300 μm on the printed wiring board 50 is applied with a 100 V, 50 kHz AC voltage. Then, when an output signal of the operational amplifier 49 was passed through a bandpass filter to extract a 50 kHz component which was applied to an oscilloscope 54, a signal synchronized with the AC voltage applied to the wire 52 was observed.

APPLICATION EXAMPLE 2

Figure 7:
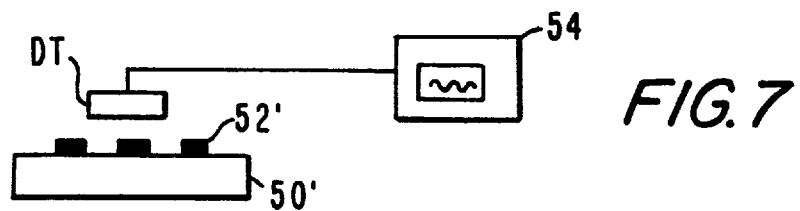
FIG. 7 is a diagram illustrating an arrangement of the detecting apparatus of the present invention when applied to detecting defects on a simple matrix type liquid-crystal display panel.

As illustrated in FIG. 7, the detecting apparatus DT of FIG. 5 was positioned such that the sensor 100 was placed above a simple matrix type liquid-crystal display panel 50' in close approximation without contacting the same, a transparent electrode 52' having a width of 300 μm on the simple matrix type liquid-crystal display panel was applied with a 10 V, 60 kHz AC voltage, and an output signal of the operational amplifier 49 was observed by the oscilloscope 54. A signal synchronized with the AC voltage applied to the transparent electrode 52' was observed.

APPLICATION EXAMPLE 3

Figure 8:
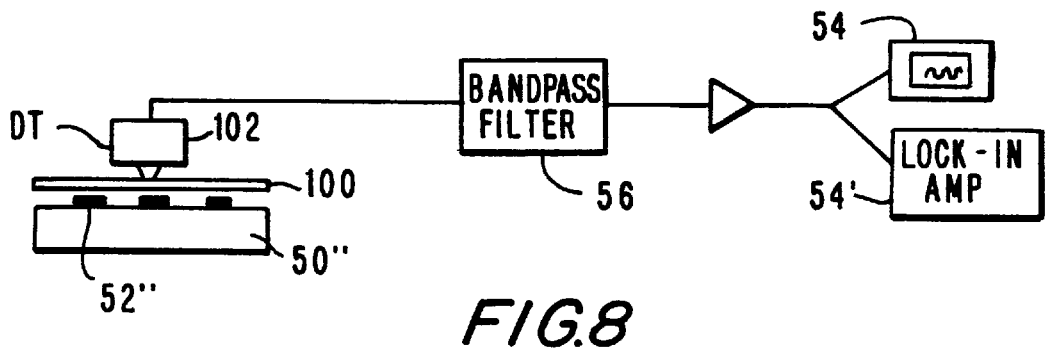
FIG. 8 is a diagram illustrating an arrangement of the detecting apparatus of the present invention when applied to detecting defects of a package for an integrated circuit.

As illustrated in FIG. 8, the optical sensor 100 and the sensor head 102 of the detecting apparatus DT were separated, and the optical sensor 100 was fixed at a working distance of 3 mm from the tip of the sensor head 102, and an ITO layer was connected to a wire as a ground electrode. The detecting apparatus DT was positioned such that the optical sensor 100 was in a close approximation to a package 50" for an integrated circuit (for example, PGA) but without contacting the same, and an electrode 52" was applied with a 100 V, 70 kHz AC voltage. A signal generated at that time from the operational amplifier 49 was passed through a bandpass filter 56 to extract a voltage component at 70 kHz. When the voltage component was amplified and then passed through the oscilloscope 54 and a lock-in amplifier 54', a signal synchronized with the AC voltage applied to the electrode 52" was observed.

APPLICATION EXAMPLE 4

In place of the light source 30 and the photoelectric transducer 46 in FIG. 5, a detecting apparatus using a photo-reflector 48 (made of Hamamatsu Photonics, P2826), as illustrated in FIG. 4, was created, and similar measurements as Application Example 1–Application Example 3 were made. As a result, signals synchronized with the AC voltages applied to the wire 52, the transparent electrode 52', and the electrode 52" were observed.

APPLICATION EXAMPLE 5

Figure 9:
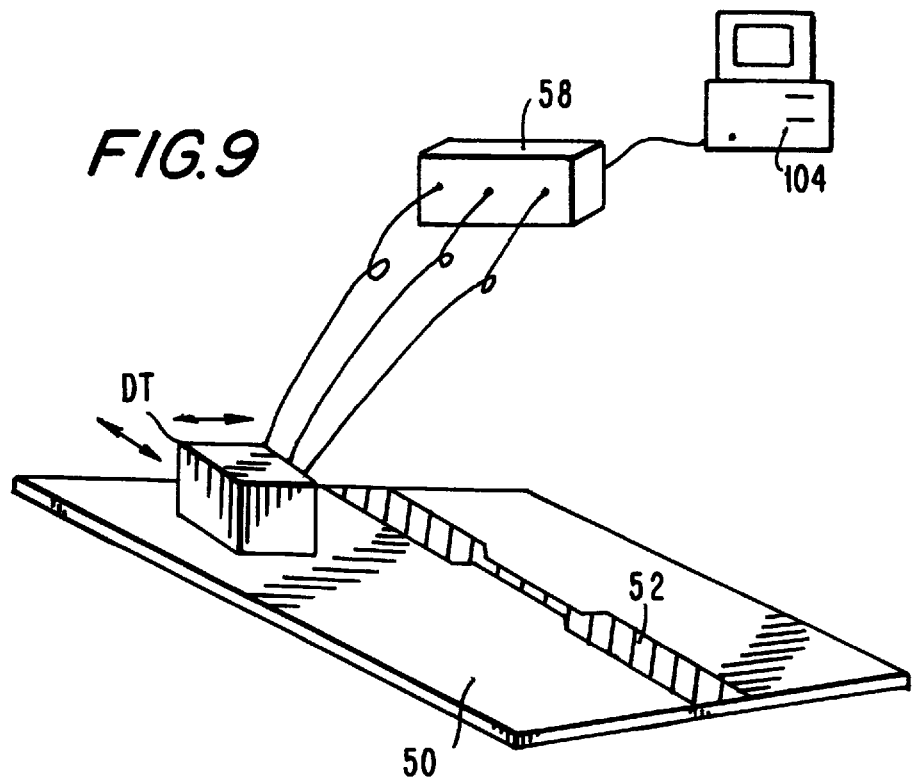
FIG. 9 is a diagram illustrating an arrangement of the detecting apparatus of the present invention when applied to detecting narrower wires on a printed wiring board.

A narrower wire 52 on a printed wiring board was detected by the detecting apparatus DT of the present invention. This application example used a detecting apparatus having light converging lenses positioned on the exit side of the λ/4 wavelength plate 38 and on the incident side of the analyzer 44 in the sensor head 102 in FIG. 5. The converging lenses converged laser light from the light source 30 into approximately 10 μm. For this application example, as shown in FIG. 9, a wire having a width of 250 μm on the printed wiring board 52 was partially formed with a narrower portion having a width of approximately 50 μm. The wire 52 was applied with a 100 V, 80 kHz AC voltage. A plane moving apparatus having an accuracy of ±1 μm was used to move the detecting apparatus DT maintained close to the printed wiring board 50 to scan the printed wiring board 50, and each position of the detecting apparatus DT was read by an encoder.

Figure 10:
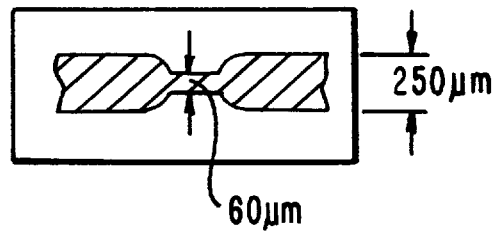
FIG. 10 is a diagram illustrating an image produced for a wire on the printed wiring board of FIG. 9.

A signal outputted at that time from the detecting apparatus DT was passed through a bandpass filter, and its output and a positional information signal of the detecting apparatus DT from the encoder were converted into digital signals by an A/D convertor 58 and then processed by the signal processing unit 104 such as a computer or the like to display as an image on a display. FIG. 10 illustrates an example of the image displayed on the display. In this application example, when data obtained from the narrower portion of the wire 52 was processed by the signal processing unit 104, it was revealed that the narrower portion of the wire 52 had FWHM (Full Width at Half Maximum) of the width equal to 61 μm.

APPLICATION EXAMPLE 6

Figure 11:
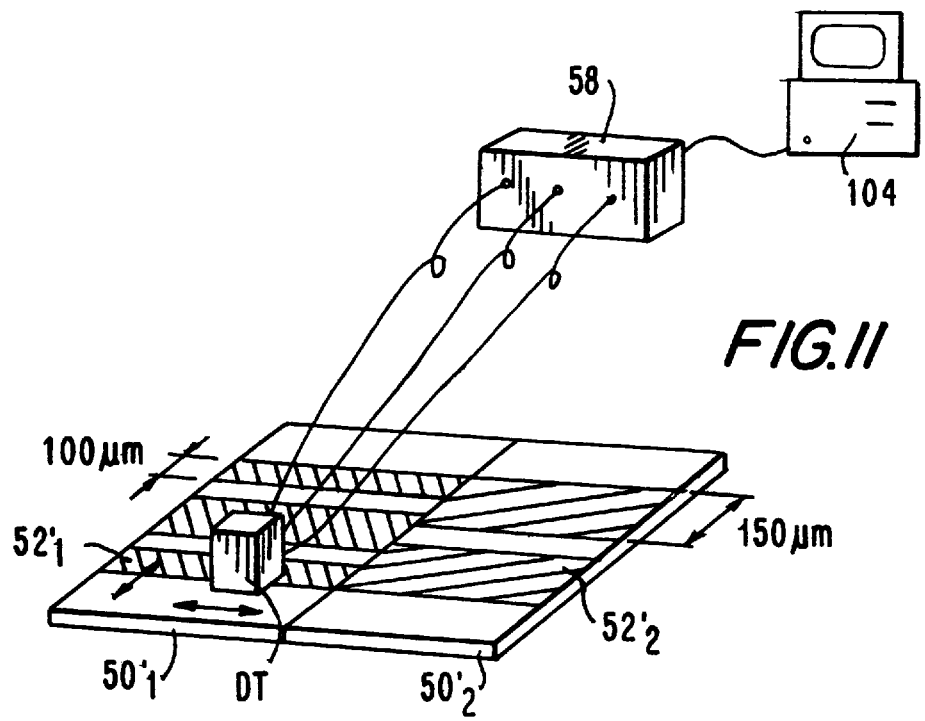
FIG. 11 is a diagram illustrating an arrangement of the detecting apparatus according to the present invention when applied to detecting narrower wires on a simple matrix type liquid-crystal display panel.

In place of the printed wiring board of Application Example 5, narrower portions of transparent electrodes were detected for a simple matrix type liquid-crystal display panel. As illustrated in FIG. 11, a simple matrix type liquid-crystal display panel 50$_1$' having transparent electrodes 52$_1$' of 100 μm in width and a simple matrix type liquid-crystal display panel 50$_2$' having transparent electrodes 52$_2$' of 150 μm in width were arranged adjacent to each other to virtually form a liquid-crystal display panel having transparent electrodes with narrower portions. The same detecting apparatus DT as that used in Application Example 5 was used, and laser light from the light source 30 was converged into approximately 10 μm by the light converging lenses. The liquid-crystal display panel is scanned by the detecting apparatus DT using a plane moving apparatus having an accuracy of ±1 μm, and each position of the detecting apparatus DT was read by an encoder.

Figure 12:
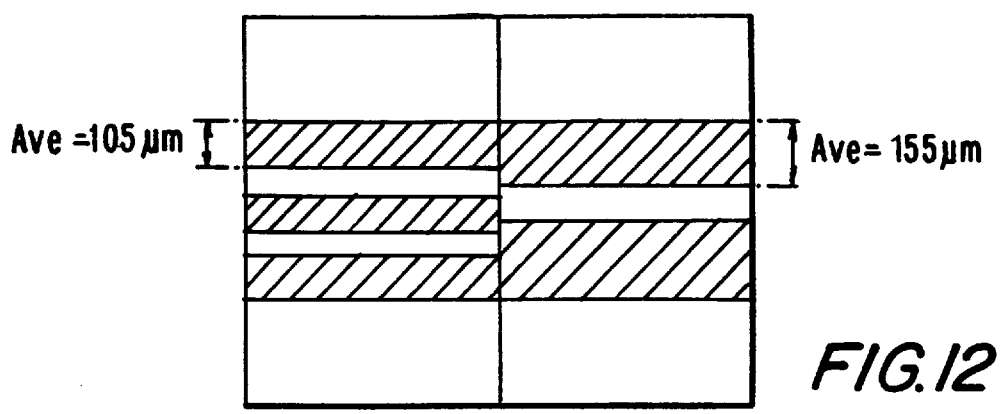
FIG. 12 is a diagram illustrating an image produced from the simple matrix type liquid-crystal display panel by the arrangement of FIG. 11.

The transparent electrodes 52$_1$', 52$_2$' were applied with a 100 V, 90 kHz AC voltage, and a signal outputted from the detecting apparatus DT at that time was passed through a bandpass filter. The output, together with a positional information signal of the detecting apparatus DT from the encoder, were converted into digital signals by the A/D convertor 58. The outputs were processed by the signal processing unit 104 such as a computer or the like to display as an image on the display. FIG. 12 illustrates an example of the image displayed on the display. It was revealed from data on transparent electrodes corresponding to a narrower portion and thicker portions in the image that the narrower portion and the thicker portions had FWHM of the width equal to 119 μm and 182 μm, respectively. From this, the detecting apparatus DT of the present Invention was confirmed to be effective in detecting narrower portions of transparent electrodes on a simple matrix type liquid-crystal display.

APPLICATION EXAMPLE 7

Figure 13:
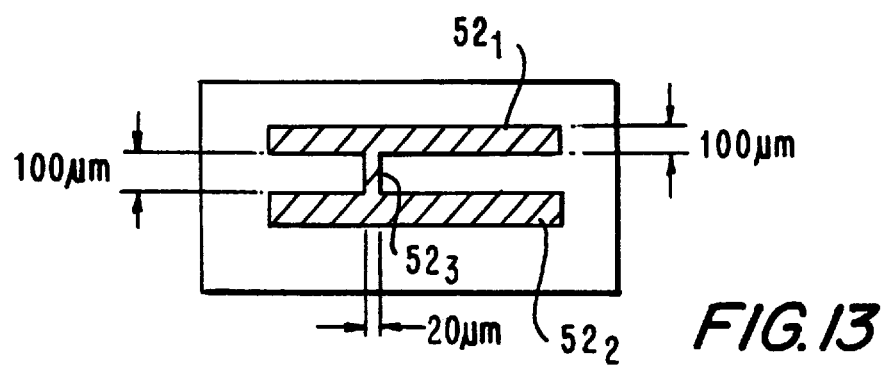
FIG. 13 is a diagram illustrating a wiring pattern used for a measurement for detecting short-circuited wires by the detecting apparatus according to the present invention.

Short-circuited wires were detected using the same detecting apparatus DT as that used in Application Example 3. For this purpose, as shown in FIG. 13, two wires 52$_1$, 52$_2$ having a width of 100 μm were formed with a gap of 100 μm therebetween, and these wires were short-circuited by a wire 52$_3$ having a width of 20 μm. One of the wires 52$_1$ only was applied with a 100 V, 100 kHz AC voltage. Similarly to Application Example 6, a signal outputted from the detecting apparatus DT at that time was passed through a bandpass filter. Then, together with a positional information signal of the detecting apparatus DT from the encoder, these outputs were converted into digital signals by the A/D convertor 58, and subsequently the outputs were processed by the signal processing unit 104 to be displayed as an image on the display. As a result, an image of the other wire 52$_2$, which had not been applied with a voltage, was also displayed on the display, thus confirming that short-circuit between both wires was occurring.

APPLICATION EXAMPLE 8

Figure 14:
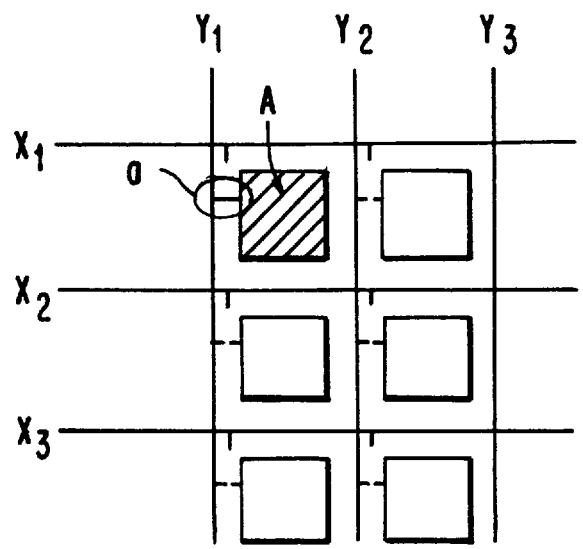
FIG. 14 is a diagram representing an image of a simulated liquid-crystal display panel used for a measurement for detecting short-circuit between electrodes of TFT on a TFT-active matrix type liquid-crystal display panel by the detecting apparatus of the present invention.

The detecting apparatus DT illustrated in FIG. 5 was used to make a measurement for detecting the presence or absence of short-circuit between a source and a drain and between a gate and a drain on a TFT-active matrix type liquid-crystal display panel. As a simulated liquid-crystal display panel used for this purpose, a panel was such that scan electrodes (gate lines) X1, X2, X3 and signal electrodes (source lines) Y1, Y2, Y3, having a width of 100 μm were arranged in an array form, and a transparent pixel electrode A and the signal electrode Y1 were connected by a thin wire, as illustrated in a, to cause short-circuit between a signal electrode (source line) or a drain line and the pixel electrode. Then, the signal electrode Y1 was applied with a 5 V, 70 kHz AC voltage, and the panel was scanned by the detecting apparatus DT. A signal generated from the detecting apparatus at that time was passed through a bandpass filter. Then, together with a positional information signal from an encoder, these outputs were converted into digital signals by the A/D convertor 58. Then, the outputs were processed by the signal processing unit 104 to display as an image on the display. The image produced by this measurement is illustrated in FIG. 14. It was confirmed that a potential was present on the pixel electrode A short-circuited with the signal electrode Y1 in this application example.

APPLICATION EXAMPLE 9

Figure 15:
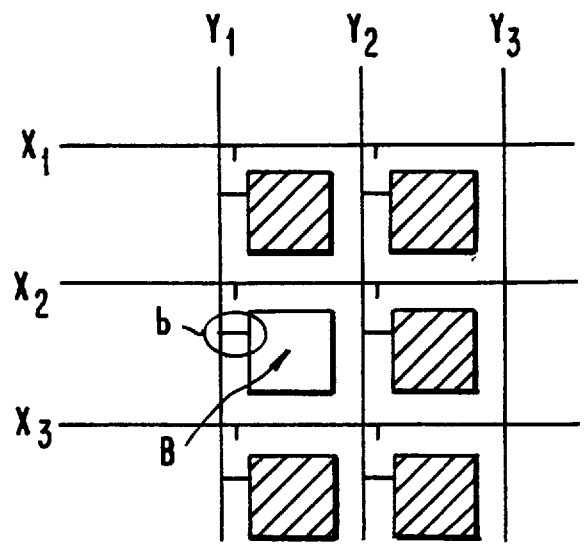
FIG. 15 is a diagram representing an image of a simulated liquid-crystal display panel used for a measurement for detecting disconnection between electrodes of TFT on a TFT-active matrix type liquid-crystal display panel by the detecting apparatus of the present invention.

Short-circuit between a source and a gate of TFT, short-circuit at an intersection of a signal electrode and a scan electrode, and a disconnected electrode at an arbitrary point on an LCD panel were detected. When such defects occur, it is thought that even if a normal voltage is applied to supply the voltage to a pixel electrode, the pixel electrode will not be actually supplied with the voltage. Thus, this application example employed a simulated panel in which all pixel electrodes were connected to corresponding signal electrodes Y1, Y2, Y3 with wires and a wire to a pixel electrode B among them was disconnected as illustrated in b. Then, a signal generated from the detecting apparatus DT when the signal electrode Y1 was applied with a 5 V, 70 kHz AC voltage, was passed through a bandpass filter. Then, together with a positional information signal from an encoder, these outputs were converted into digital signals by the A/D convertor 58, and the outputs were processed by the signal processing unit 104 to display as an image on the display. FIG. 15 illustrates the image produced at that time. It was confirmed that no potential was present on the pixel electrode B in this application example.

APPLICATION EXAMPLE 10

A measurement was made by the detecting apparatus DT as to whether or not short-circuit occurred by break-down during a break-down test on a printed wiring board having two wires having a width of 100 μm formed with a gap of 1 μm therebetween. For this purpose, one of these wires was applied with a 1 kHz AC voltage, and the detecting apparatus DT was scanned on the printed wiring board as the voltage was increased from 50 V to 500 V. It was observed that at about 450 V, the wires were short-circuited due to break-down, and that a voltage was generated also on the wire which had not been applied with the voltage.

APPLICATION EXAMPLE 11

The wire 52 on the printed wiring board 50 of FIG. 9 was partially disconnected, and the detecting apparatus DT used in Application Example 5 was employed to conduct an experiment for detecting the disconnected wire on the printed wiring board. The wire 52 was applied with a 5 V, 70 kHz AC voltage, the detecting apparatus DT was scanned on the printed wiring board 50, an output signal of the detecting apparatus DT was passed through a bandpass filter and subsequently converted into a digital signal by an A/D convertor, and this digital signal was processed by the signal processing unit 104 to display it on the display. A data comparison between the displayed wiring pattern and the original wiring pattern allowed the disconnected location to be detected.

APPLICATION EXAMPLE 12

Figure 16:
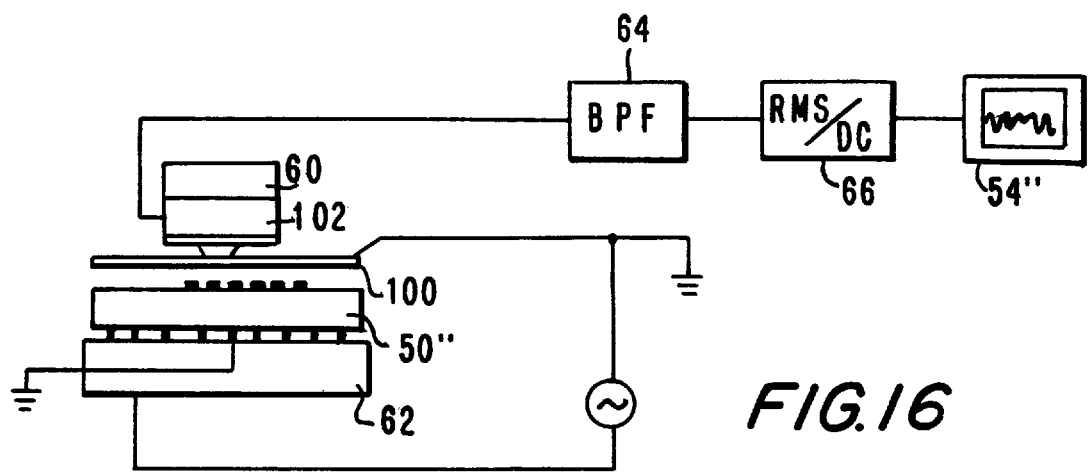
FIG. 16 is a diagram illustrating an arrangement of the detecting apparatus according to the present invention when applied to the detection of disconnected wires in a package for an integrated circuit.
Figure 17:
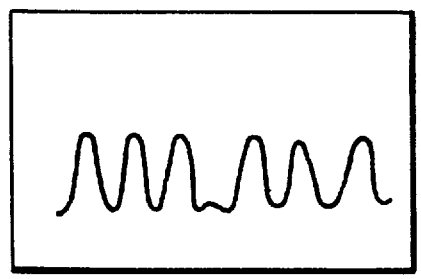
FIG. 17 is a diagram illustrating a pattern produced by the detecting apparatus in the arrangement of FIG. 16.

As illustrated in FIG. 16, disconnected wires in a package 50" for an integrated circuit were detected using the detecting apparatus DT having the separated sensor head 102 and optical sensor 100 and a moving apparatus 60 for moving the sensor head 102 in one direction. The optical sensor 100 was diced to a size of 10×10 mm and fixed close to the package 50" for an integrated circuit, and its ground electrode was grounded with a wire. In this case, since a signal level lowers as a gap between the optical sensor 100 and the package 50" for an integrated circuit is larger, sufficient attention should be paid for setting the gap. For virtually creating a disconnected location, proper electrodes in the package 50" for an integrated circuit were grounded and prevented from being applied with an AC voltage, and a voltage applying unit 62 was connected to the package 50" for an integrated circuit to apply a 100 V, 70 kHz AC voltage to electrodes, which were not grounded, from the pin side. In this way, as the sensor head 102 was moved over the package 50" for an integrated circuit by the moving apparatus 60 at a speed of 5 mm/second, reflected light from the optical sensor 100 was transduced into an electrical signal and amplified in the sensor head 102, and a 70 kHz signal component only was extracted by a bandpass filter 64. The extracted signal component was converted into a DC form by an RMS/DC convertor 66, and a signal strength of the 70 kHz signal component was displayed on a storage type oscilloscope 54". FIG. 17 illustrates an example of the pattern thus displayed, where the abscissa represents the time, while the ordinate represents the signal strength. This pattern shows that no signal is generated from electrodes which are not applied with the AC voltage (grounded), so that it was confirmed that a disconnected location on a wire could be detected by a data comparison between the displayed pattern and the original wiring pattern. It was also revealed that FWHM was 102 μm on an average and was coincident with the actual wire width.

APPLICATION EXAMPLE 13

Figure 18:
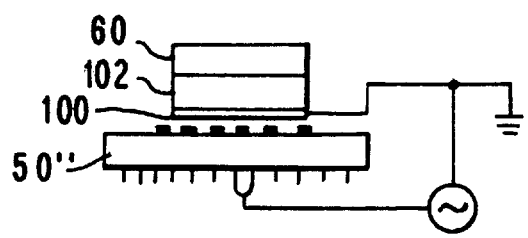
FIG. 18 is a diagram illustrating an arrangement of the detecting apparatus according to the present invention when applied to the detection of short-circuit in a package for an integrated circuit.
Figure 19:
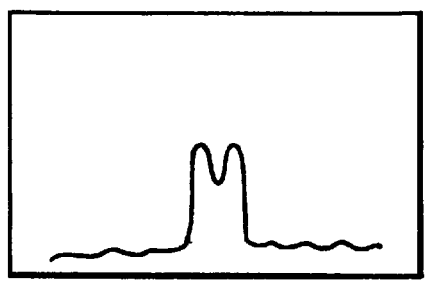
FIG. 19 is a diagram illustrating a pattern produced by the detecting apparatus in the arrangement of FIG. 18.

The detecting apparatus DT illustrated in FIG. 5 was used to make a measurement for detecting the presence or absence of short-circuited locations in the package 50" for an integrated circuit. For this purpose, arbitrary two pins in the package 50" for an integrated circuit were connected with a wire to short-circuit them, as illustrated in FIG. 18, and one of these pins was applied with an AC voltage. Then, the detecting apparatus DT was moved on the package 50" for an integrated circuit by the moving apparatus 60, and a signal generated by the detecting apparatus DT was similarly processed to display it on the display, with the result that a pattern illustrated in FIG. 19 was produced, where the abscissa represents the time, while the ordinate represents the signal strength. It was confirmed from this pattern that short-circuited electrodes could be detected.

INDUSTRIAL AVAILABILITY

As will be understood from the detailed description of the present invention based on several embodiments, the present invention produces remarkable effects that the existence and occurring locations of defects such as disconnected wires, narrower wires and short-circuit on a variety of wiring boards such as printed wiring boards, liquid-crystal display panels, packages for integrated circuits, and so on can be detected in a non-contact manner and in a short time. In addition, the present invention, when applied to a multiple-layer printed wiring board, produces a remarkable effect that defects existing on all layers can be simultaneously detected. Further, the detection of defects on a liquid-crystal display panel can be accomplished even if an orientation film is coated.

We claim:

1. A detecting apparatus for detecting defects of wires on a wiring board including at least one layer of wires, characterized by comprising:

an optical sensor including a transparent substrate, a transparent electrode disposed on said transparent electrode, a film of a polymer non-linear optical material disposed on said transparent electrode, and a reflective film disposed on said film, and positioned close to a wire to be measured on said wiring board and without contacting same;

a sensor head including a light source, optical means for guiding light from said light source into said optical sensor, and detecting means for detecting reflected light from said optical sensor to derive a signal corresponding to the intensity of said reflected light when said wire is applied with a voltage; and a processing unit for processing said signal derived from said detecting means to output a signal corresponding to the presence or absence of a defect on said wire.

2. A detecting apparatus according to claim 1, characterized in that said polymer non-linear optical material has a structure expressed by the following formula I or formula II:

 (I)

 $(l \geq 1, m \geq 0, n \geq 0)$ (II)

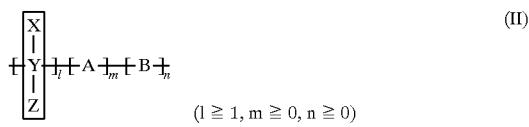 $(l \geq 1, m \geq 0, n \geq 0)$ where P is a main chain of a non-linear optical active copolymer, S is a spacer group comprising a direct coupling or a straight-chain hydrocarbon radical having a number of carbon atoms ranging from 1 to 20, [X—Y—Z] is a chromophore having a non-linear optical activity, X is an electron donative group, Y is a π-electron conjugated system, Z is an electron attractive group, A is a copolymer unit which has no non-linear optical activity, and B is a copolymer unit and/or a functional copolymer unit having another function.

3. A detecting apparatus according to claim 2, characterized in that said main chain unit P is a polyvinyl system, a polysiloxane system, polyoxyalkylene system, a polyvinylidene system, a polyurethan system, a polytriazine system, a polyester system, or a polyamide system.

4. A detecting apparatus according to claim 1, characterized in that said optical sensor and said sensor head are integrated.

5. A detecting apparatus according to claim 1, characterized in that said optical sensor and said sensor head are separated.

6. A detecting apparatus according to claim 5, characterized in that the dimension of said optical sensor is substantially equal to the dimension of said wiring board.

7. A detecting apparatus according to claim 1, characterized in that said defects on wires are narrower or disconnected wires, short-circuit between said wires, or any combination thereof.

8. A detecting apparatus according to claim 1, characterized in that light incident to said optical sensor 1 by said optical means is linear or planar.

9. A detecting apparatus according to claim 1, characterized in that a voltage applied to said wires has a frequency ranging from 50 kHz to 100 kHz.

10. A detecting apparatus according to claim 1, characterized in that said wiring board is a printed wiring board.

11. A detecting apparatus according to claim 10, characterized by simultaneously detecting defects on wires on each of layers of said multiple-layer printed wiring board.

12. A detecting apparatus according to claim 1, characterized in that said wiring board is a liquid-crystal display panel.

13. A detecting apparatus according to claim 12, characterized in that said liquid-crystal display panel is a simple matrix type panel.

14. A detecting apparatus according to claim 12, characterized in that said liquid-crystal display panel is an active matrix type panel.

15. A detecting apparatus according to claim 12, characterized in that said defects of wires are detected in a condition where said liquid crystal display panel is coated with an orientation film.

16. A detecting apparatus according to claim 1, characterized in that said wiring board is a package for an integrated circuit.

17. A detecting apparatus according to claim 16, characterized in that said package for an integrated circuit is any one of PGA, PPGA, BGA, and PBGA.

\* \* \* \* \*